US009399050B2

(12) United States Patent
Stamets (10) Patent No.: US 9,399,050 B2
(45) Date of Patent: *Jul. 26, 2016

(54) CONTROLLING INSECTS AND ARTHROPODS USING PRECONIDIAL MYCELIUM AND EXTRACTS OF PRECONIDIAL MYCELIUM FROM ENTOMOPATHOGENIC FUNGI

(71) Applicant: Paul Edward Stamets, Shelton, WA (US)

(72) Inventor: Paul Edward Stamets, Shelton, WA (US)

( * ) Notice: Subject to any disclaimer, the term of this patent is extended or adjusted under 35 U.S.C. 154(b) by 93 days.

This patent is subject to a terminal disclaimer.

(21) Appl. No.: 13/986,978

(22) Filed: Jun. 20, 2013

(65) Prior Publication Data

US 2013/0287829 A1 Oct. 31, 2013

Related U.S. Application Data

(60) Continuation-in-part of application No. 13/066,566, filed on Apr. 18, 2011, now Pat. No. 8,501,207, which is a division of application No. 12/288,535, filed on Oct. 20, 2008, now Pat. No. 7,951,389, which is a division of application No. 10/853,059, filed on May 24, 2004, now abandoned, which is a division of application No. 09/959,456, filed on Oct. 1, 2001, now Pat. No. 7,122,176, which is a continuation-in-part of application No. 09/678,141, filed on Oct. 4, 2000, now Pat. No. 6,660,290.

(51) Int. Cl.
*A61K 36/07* (2006.01)
*A61K 35/644* (2015.01)
*A61K 45/06* (2006.01)
*A01N 63/04* (2006.01)
*A01N 65/00* (2009.01)

(52) U.S. Cl.
CPC .............. *A61K 36/07* (2013.01); *A01N 63/04* (2013.01); *A01N 65/00* (2013.01); *A61K 35/644* (2013.01); *A61K 45/06* (2013.01)

(58) Field of Classification Search
None
See application file for complete search history.

(56) References Cited

U.S. PATENT DOCUMENTS

| 6,660,290 | B1 * | 12/2003 | Stamets | A01N 63/04 424/195.15 |
|---|---|---|---|---|
| 7,951,388 | B2 * | 5/2011 | Stamets | 424/405 |
| 7,951,389 | B2 * | 5/2011 | Stamets | 424/406 |
| 8,501,207 | B2 * | 8/2013 | Stamets | 424/406 |

* cited by examiner

*Primary Examiner* — Carlos Azpuru
*Assistant Examiner* — Casey Hagopian
(74) *Attorney, Agent, or Firm* — William R. Hyde (57) ABSTRACT

The present invention utilizes the pre-sporulation (preconidial) mycelial stage of entomopathogenic fungi and extracts of the preconidial mycelium as insect and arthropod attractants and/or pathogens. The preconidial preparations can be employed to limit the zoonotic and plant diseases they transmit. The fungus can be cultivated on grain, wood, agricultural wastes or other cellulosic material and extracts can be made thereof. More than one fungus and substrate can be used in combination with one or more antimicrobial, antiprotozoal, antiviral, or genetically modified agents that result in reduced spread of contagions and lessens the damage they inflict on animals and plants.

6 Claims, 3 Drawing Sheets

**Attractancy of Fungus Gnats to Extracts of Preconidial Mycelium of *Metarhizium anisopliae* Grown on Rice, Compared to Extracts of Rice Without Mycelium**

■ Control   ▫ *Metarhizium anisopliae* (Entomopathogenic fungus)

Figure 3

CONTROLLING INSECTS AND ARTHROPODS USING PRECONIDIAL MYCELIUM AND EXTRACTS OF PRECONIDIAL MYCELIUM FROM ENTOMOPATHOGENIC FUNGI

CROSS-REFERENCE TO RELATED APPLICATIONS

This application is a continuation-in-part of U.S. patent application Ser. No. 13/066,566, filed Apr. 18, 2011, currently co-pending, which is a divisional of U.S. patent application Ser. No. 12/288,535, filed Oct. 20, 2008 (now issued as U.S. Pat. No. 7,951,389), which is a divisional of U.S. patent application Ser. No. 10/853,059, filed May 24, 2004, which is a divisional of U.S. patent application Ser. No. 09/969,456, filed Oct. 1, 2001 (now issued as U.S. Pat. No. 7,122,176), which is a continuation-in-part of U.S. patent application Ser. No. 09/678,141, filed Oct. 4, 2000 (now issued as U.S. Pat. No. 6,660,290), all of which are incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The present invention relates to mycology, entomology, and the use of preconidial preparations of entomopathogenic fungi as attractants (mycoattractants) and biopesticides (mycopesticides, mycoinsecticides) in combination with other technologies to control, decrease, limit or prevent the spread of diseases carried by insects and/or other arthropods. More particularly, the invention relates to the control of zoonotic diseases and plant diseases by attracting, or attracting and killing, insects, including ants, flies, beetles, cockroaches, bed bugs, mosquitoes, grasshoppers, flies and other arthropods such as ticks, mites, midges, lice and fleas, using pre-sporulating mycelia of entomopathogenic fungi and extracts of pre-sporulating mycelia.

2. Description of Related Art Including Information Disclosed Under 37 CFR 1.97 and 1.98

Diseases emanating from ecologically distressed and polluted environments increasingly threaten animals and plants. With deforestation, habitat destruction, decline in water quality and decreases in biodiversity, all of which are exacerbated by global climate change and human impacts, zoonotic diseases are increasingly a threat to healthy environments and their inhabitants, especially animal populations, including humans and their livestock. Many of these disease-causing organisms are carried by or bred within insects or other arthropods. Insects are any of the large class (Insecta) of small arthropod animals characterized, in the adult state, by division of the body into head, thorax, and abdomen, three pairs of legs on the thorax, and, usually, two pairs of membranous wings; arthropods are any of the largest phylum (Arthropoda) of invertebrate animals with jointed legs, a segmented body, and an exoskeleton, including herein insects, arachnids such as spiders, mites and ticks, and myriapods. Since many of these bite humans and livestock, as well as damage plants, they transmit a wide variety of diseases, many of which result in billions of dollars worth of damage to economies worldwide.

Insects are among the most diverse and numerous life forms on earth. While the majority of the one million named species of insects are considered beneficial, somewhere from 1% to 5% are considered to be pests. Some of these insect pests not only cause tremendous losses in terms of direct destruction of crops, livestock, and human dwellings, they are also vectors for pathogens including protozoa, round worms, fungi, bacteria, and viruses that cause devastating human health problems. As climates change, with an overall tendency to warming, tropical and subtropical diseases are spreading into temperate regions, once devoid of these threats. The negative physical, mental, economic, social and ecological implications of disease carrying pest insects and arthropods are difficult to quantify since their effects are wide-ranging and multidimensional. As ecosystems in which humans dwell are harmed, water is polluted, sanitation hurdles mount, toxins are accumulated and food scarcity increases, animals (including humans) become much more susceptible to infection from pathogen-carrying insects and arthropods as their innate immune systems are weakened. Chemical pesticides, antibiotics, and vaccinations are notoriously ineffective against long-term exposure to populations of rapidly evolving organisms. Additionally, resistance to pesticides and antimicrobials can result in "super-bugs" which often develop in both insects and arthropods, as well as in the microbes they transmit. As diseases ebb and flow, we need a more sophisticated way of out-smarting the vectors that carry them. If the vector can be stopped, the disease can be stopped. By using attractants from entomopathogenic fungi, this new approach allows the unusual flexibility of being able to switch or combine attractant extracts and mycelium sourced by tapping into the vast and continually evolving genome of naturally occurring wild or human-improved strains.

Many insects and arthropods are vectors for contagions. Some in particular are common carriers of pathogens and contagions. Many of these contagions are spread by simple contact, some are spread from bites or proboscis punctures, while others can be transmitted to animals when they consume these disease-laden insects.

Zoonotic disease is defined as any disease that is spread from animals to people. The use of preconidial entomopathogenic fungi, and extracts and derivatives thereof, can also prevent non-zoonotic diseases, such as those transmitted to plants, including bacteria, fungi and viruses, which are also anticipated by the inventor. Any subsequent insect and arthropod controlling technology can be enhanced since the insects and arthropods become concentrated as a result of the attractant properties of the preconidial mycelium or extract of selected entomopathogenic fungi. A further novelty of this invention is that it allows other technologies that limit disease to work more effectively by concentrating and localizing the disease-spreading organism to a more centralized locus, reducing expenses while enhancing efficacies. In essence, disease vectors by insects and arthropods can be better controlled.

Mites and other arthropods can carry diverse populations of pathogenic bacteria, protozoa and viruses. For instance, ticks carry *Borrelia* species bacteria causing Lyme disease. In North America, *Borrelia burgdorferi* is a Gram-negative spirochete bacteria that is well known as the causative agent of Lyme disease. In Europe, *Borrelia afzelii* and *Borrelia garinii* are the bacteria known to transmit this disease. These bacteria, and likely more species yet to be discovered, spread to humans and animals by bites from ticks, especially species of ticks of the genus *Ixodes*. The western black-legged tick, *Ixodes pacificus*, in the western United States and the deer tick *Ixodes scopularis* (=*Ixodes dammini*) in the eastern United States are the primary species vectoring *Borrelia* bacteria to humans and other animals. Ticks in the genus *Ixodes*, such as *I. scopularis*, can also vector protozoa (from *Babesiosis* species), causing "Nantucket fever", and some viruses, including encephalitis. More types of pathogens vectored by ticks are likely to be detected as research continues to track zoonotic and plant diseases.

Pharaoh Ants, *Monomorium pharaonis* and related species, are known as vectors to more than dozen pathogenic bacteria, including *Salmonella* spp., *Staphylococcus* spp., and *Streptococcus* spp., and are especially dangerous to burn victims recovering in hospital environments. See Beatson S. H., "Pharaoh ants as pathogen vectors in hospitals," Lancet 1: pp. 425-427 (1972); Haack K. D., Granovsky T. A., Ants, In Handbook of Pest Control, Story K. and Moreland D. (eds.), Franzak & Foster Co., Cleveland, Ohio. pp. 415-479 (1990); and Smith E. H., Whitman R. C., Field Guide. Structural Pests, National Pest Management Association, Dunn Loring, Va., (1992).

Similarly, bed bugs can vector these same bacterial pathogens, endangering humans, typically while they sleep. Christopher F. Lowe and Marc G. Romney (Volume 17, Number 6—June 2011 in the Centers for Disease Control, *Emerging Infectious Diseases, Letters*, "Bedbugs as Vectors for Drug-Resistant Bacteria" reported that bed bugs vector methicillin-resistant *Staphylococcus aureus* (MRSA) and vancomycin-resistant *Enterococcus faecium* (VRE) from bedbugs in Vancouver, British Columbia. Not surprisingly, the inventor anticipates many other bacterial, viral or protozoan diseases are likely to be discovered that are spread by these biting arthropods.

Below is a short summary of insects and arthropods with some of the zoonotic pathogens they transmit.

Arthropods Vectoring Zoonotic Pathogens

Bed Bugs: MRSA (methicillin resistant *Staphylococcus aureus* and *Enterococcus faecium* bacteria) carried by *Cimex* species; other bacteria.

Lice and ticks: Bacteria, including *Rickettsia* spp. causing Rocky Mountain Spotted fever; *Bartonella vinsonii* and *B. henseiae* causing intramuscular infections; and *Borrelia burgdorferi*, *Borrelia afzelii* and *Borrelia garinii* causing Lyme disease. Colorado tick fever, also called American mountain tick fever, is a viral infection transmitted from the bite of an infected *Dermacentor andersoni* tick. Powassan, a minor cause of viral encephalitis.

Mosquitoes: Malaria, Arboviral Encephalitides (viral diseases causing brain inflammation/encephalitis including West Nile virus, Japanese encephalitis, La Crosse encephalitis, St. Louis encephalitis, Eastern equine encephalitis and Western equine encephalitis), Dengue fever, Yellow fever, Rift Valley fever, dog heartworm.

Flies: Diseases carried by or transmitted by flies including typhoid, cholera, dysentery, infantile or summer diarrhea, pinkeye, *salmonella*, anthrax and tuberculosis. Tsetse flies transmit African trypanosomiasis (human sleeping sickness caused by *Trypanosoma brucei*). Sandflies transmit Chandipura virus.

Fleas: Bacteria, including *Yersinia pestis* causing bubonic plague, murine or endemic typhus, and *Bartonella henselae*, viruses including myxomatosis, reckettsial diseases, helminth (*Hymenolepiasis* tapeworm), trypanosome protozoa.

Triatomid bugs: Chagas disease (South American trypanosomiasis, *Trypanosoma cruzi*).

Midges: Viruses (Blue tongue virus to cattle, epizootic hemorrhagic disease).

Leafhoppers: Tomato/Tobacco Mosaic viruses, wheat striate mosaic virus, maize fine streak virus, chickpea chlorotic dwarf virus, green petal virus and others.

Virtually all biting insects and arthropods can result in bacterial or viral infections, either directly from a contagion reservoir within them or from wound exposure to the open environment. This is true with regard to both animal and plant diseases.

The present invention affords yet another new option for disease control: to attract but not necessarily kill arthropods, whilst reducing or eliminating their pathogen payloads. This option is important especially in areas where the arthropod populations are helpful in maintaining biological diversity of other animals that are dependent upon them for food. Removing all the arthropods from an ecosystem would likely result in unforeseen consequences, beyond that which is readily obvious. The food web is interconnected, and while most experts will agree that reducing disease vectors is prudent, destroying a native insect population is not.

Moreover, since *Metarhizium* and other entomopathogenic fungi are natural parasites of many arthropods, the natural genome of these fungal species offer sources of ever-evolving libraries of new strains, making resistance much more unlikely compared to chemical pesticides. An additional advantage of using preconidial entomopathogenic fungi such as *Metarhizium anisopliae* is that native strains of this fungus can be isolated wherever arthropods live, meaning that the constant co-evolution of this fungus to overcome resistance factors of the arthropods provides us with a unique partnership with nature to constantly adapt native, new strains of this fungus for implementation in controlling arthropods. Moreover, if new strains of *Metarhizium anisopliae* are blended with any antimicrobial or antiviral agent, the arthropods and the diseases they spread can be further controlled. Should the disease organism being carried by, for instance, a tick, develop resistance to an antimicrobial or antiviral drug, then a mixture of more than one drug or remedy can be employed to overcome resistance. Thus, this invention allows for a platform for continually out-evolving resistance by blending technologies and combining antimicrobials—out-racing the ability of arthropods and pathogens to adapt to either the entomopathogenic fungus or the antimicrobial method employed at the points of contact. Such synergism can have many derivative improvements and are expected by this inventor.

An example would be to blend the mycoattractive extracts and/or mycelia of preconidial entomopathogenic fungi attractive to arthropods with antiviral prodrugs, the less expensive antiviral drug precursors, expired antiviral drugs, or drugs such as Abacavir, Aciclovir, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Famciclovir, Fomivirsen, Fosamprenavir, Foscarnet, Fosfonet, Ganciclovir, Ibacitabine, Immunovir, Idoxuridine, Imiquimod, Indinavir, Inosine, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir (Tamiflu), Peginterferon alfa-2a, Penciclovir, Peramivir, Pleconaril, Podophyllotoxin, Protease inhibitors, Raltegravir, Reverse transcriptase inhibitors, Ribavirin, Rimantadine, Ritonavir, Pyramidine, Saquinavir, Stavudine, Tea tree oil, Tenofovir, Tenofovir disoproxil, Tipranavir, Trifluridine, Trizivir, Tromantadine, Truvada, Valaciclovir (Valtrex®), Valganciclovir, Vicriviroc, Vidarabine, Viramidine, Zalcitabine, Zanamivir (Relenza®) and Zidovudine.

This same principle could also be used to enhance more traditional arthropod control devices. For example, blends of extracts and preconidial mycelium of entomopathogenic fungi can be used to enhance performance of bed bug control devices such as sticky mats, entanglements, piercers-and-hookers, blood or scent attractant based traps, darkened bed bug "hotel" collectors or wherever other "attract-and-trap" control mechanisms are installed. In essence, any current or future method might well result in greater performance for controlling arthropods, whether these be bed bugs, mites, ticks, mosquitoes or others, by employing extracts and mycelium of preconidial entomopathogenic fungi.

Because the purification of antimicrobial, antibacterial, antiprotozoal and antiviral drugs is typically more much expensive than their crude, or semi-pure precursors, this invention anticipates that less-than-pharmaceutical grade antimicrobial, antibacterial, antiprotozoal and antiviral medicines can be employed in combination with extracts and the mycelium of pre-conidial entomopathogenic fungi to create a successful treatment in the prevention, mitigation or curing of contagions transmitted by insects and arthropods. Moreover, the inventor's prior research on the use of polypore mushroom derivatives to combat viruses, which employ a similar method of extraction to the methods described herein for the creation of attractant preconidial entomopathogenic extracts, is yet another application of this novel way of limiting zoonotic and other forms and vectors of contagions.

Arthropods such as lice, bed bugs, mosquitoes, fleas and ticks can carry and transmit zoonotic diseases to humans and other animals, compounding the challenge faced by hospitals, hotels, homes, dormitories, army barracks, prisons and other densely populated areas. Denser populations of humans and animals—especially denser populations of immunocompromised humans and animals—increase the probably of infection and re-transmission.

Whether the initial infection being transmitted from a biting insect or arthropod is from a bacterium, a virus or a protozoan, co-occurrence of non-insect and non-arthropod borne diseases may more readily ensue. The now-lowered immunity of the infected animal population at large may, for instance, make the spread of Ebola, Hanta, bird flu viruses, diphtheria, dysentery, viral and bacterial meningitis or any contagion more readily spreadable. The resultant consequences of a population's lowered immunity can also degrade the overall population's immunological defenses against cancers. Conversely, those already suffering from cancer, or those with compromised immune systems due to other diseases, are more susceptible to infection.

Moreover, insects and arthropods spread viruses into plants. For instance, caterpillars and grasshoppers spread the Tomato-Tobacco Mosaic Virus. For farmers, there are dual advantages for controlling plant eating insects and the crop destroying diseases they spread. By combining extracts from the polypore mushroom, *Fomes fomentarius*, a source of antiviral agents active against the Tobacco Mosaic Virus with preconidial mycelium or extracts of *Cordyceps* species (well known for infecting caterpillars and grasshoppers), farmers could benefit by both limiting these crop damaging insects and lessening the threat of viruses they spread. This is but one of many examples that will become obvious and are expected manifestations of the current invention.

Hence this inventor sees a two-fold need: to control movement of insects and arthropods, and to control the pathogenic bio-burden of insects and arthropods that transmit diseases to people, animals, and plants. Combining methods and compositions discussed herein to create discrete ways to attract disease-carrying insects and subsequently killing them and/or reducing their pathogenic payloads will be important for protecting environmental health. In the age of technologies creating genetically modified organisms, potentiating pathogen carrying insects and arthropods as biological weapons is possible and protection from such threats is sorely needed. Hence, this invention could be important for defense against bioterrorism in its many elaborations.

BRIEF SUMMARY OF THE INVENTION

In view of the lack of use of the preconidial mycelium of entomopathogenic fungal mycelium to attract insects and arthropods that carry contagions and disease, the present invention provides improved insect biocontrol agents and methods and compositions of using such agents.

The present invention offers a unique approach to zoonotic disease control by attracting insects or arthropods that contact or ingest "preconidial" mycelium of entomopathogenic fungi (that is, mycelium in a developmental state prior to conidia or spore formation) which is also combined with any pest or disease controlling mechanism, another drug, plant derived medicine, pharmaceutical, hormone disrupter, attenuation gene, bacteriophage, or fungus or fungi possessing antimicrobial or anti-viral properties that results in arresting movements by such insects or arthropod while limiting the populations and pathogenicity of their carrier diseases.

Preconidial mycelium is defined as mycelium lacking spores but existing in a state prior to or without spore formation. The preconidial state and preconidial mycelium may include sclerotia or microsclerotia, compact masses of hyphae that are formed by certain fungi and give rise to new fungal growth or spore-producing structures. Commercial conidial formations of *Metarhizium anisopliae* strive to achieve at least 1,000,000 conidia per gram, and optimally 10,000,000-100,000,000+ per gram. Preconidial mycelium is defined in ranges as preferably having less than 10,000 conidia per gram of myceliated substrate, more preferably less than 1,000, and most preferably less than 100 conidia per gram. The preconidial mycelium is optimally without spores. Preconidial mycelium can be created by selectively culturing non-sporulating sectors from entomopathogenic fungi or by chemical agents that temporarily suppress conidia (spore) formation. See U.S. Pat. No. 7,951,389 and other patents by the present inventor. Either way, conidia formation can be re-activated, either naturally or artificially. Using preconidial preparations, mycelium and extracts in a variety of forms—living, frozen, dried, freeze dried, extracted—offers advantages by attracting insects or other arthropods and concentrating them into a more centralized location. Once concentrated, a variety of technologies can be deployed to trap or kill the insects and other arthropods and reduce the pathogen payload they harbor.

Such preconidial mycelium of entomopathogenic fungi may be used solely as an attractant (either as an attractant for pest insects or as an attractant for beneficial insects) or as an attractant and pathogen where the preconidial mycelium is both the attractant and the pathogenic agent. Additionally, when the insects or arthropods make contact with the preconidial entomopathogenic mycelium, there is the added advantage of reducing disease transmission by having another control technology in the same locale.

Where attractant mycopesticidal strains are utilized with insects, the infected insects carrying the fungal hyphae become a vector back into population, further dispersing the antimicrobial mycelium. The preconidial mycopesticidal mycelium can grow within or upon an insect, can be carried to another insect when they touch, or can grow upon organic debris allowing subsequent insect infestation from simple contact. Moreover, some insects will become immunocompromised from contact with *Metarhizium* or other entomopathogen based products, and the resultant lowered immunity allows for other pathogenic fungi to infect the now weakened insect. This secondary infectious suite of organisms can be more virulent than the *Metarhizium* itself. All these modes of action result in lowering the environmental bio-burden and lowering the pathogenic payloads that these zoonotic disease-bearing insects harbor.

Multiple avenues of growth and infection are provided and could be further enhanced if the addition of conidia from entomopathogenic fungi were deployed, as part of the composition of insect control. With regard to mosquitoes, recent data shows *Beauveria bassiana* spores (and to a lesser extent, *Metarhizium anisopliae* spores) are highly attractive to female *Anopheles stephensi*, a major anopheline mosquito vector of human malaria in Asia. George J., Jenkins, N E, Blanford S, Thomas M B, Baker T C (2013), Malaria Mosquitoes Attracted by *Fatal Fungus*, PLos ONE 8(5): e62632. It would not be surprising to find that attractiveness is augmented by or due to mycelial components from which the spores are harvested. Conidia harvesting equipment such as the "MycoHarvester" utilized by George et al. are designed to concentrate conidia from entomopathogenic fungi but do not completely separate hyphal fragments (fungal filaments) from the conidia in the resultant mixture and more hyphal fragments than spores may be present. Thus the attractive co-occurring fungal filaments are mixed in with the repellant spores, making this spore laden mixture attractive to insects such as mosquitoes which would be otherwise repelled by a pure spore based product.

The addition of the attractive properties of preconidial mycelium of entomopathogenic fungi may overcome or partially overcome the repellent properties of conidia (spore) based compositions, insecticides and/or miticides, thus making bait-and-trap devices such as fabric cloths or sticky mats for catching mosquitoes, gnats, flies, bed bugs, ticks and other insects and arthropods, electric bug zappers and traps for controlling termite and ants more useful for commercialization.

The preconidial mycelium of mycopesticidal fungi is grown in pure culture using standard techniques for in vitro propagation. Once inoculated onto a substrate such as grain or wood, the mycelia matures to a state prior to conidia formation. The window of utility extends from post-spore germination through all stages of mycelial growth prior to sporulation. The preconidial mycelium may be utilized as is or may be arrested in its development through means such as flash chilling, freeze-drying, air-drying, refractance window dehydration, cryogenics, refrigeration, gaseous cooling, gas affixation (nitrogen, carbon dioxide, ethylene) and packaged in spoilage-proof or sealed packages. Even with post-conidial cultures of entomopathogenic fungi, methods can be employed which will 'turn off' conidial formation and 'turn on' non-conidial mycelial growth, resulting in attractancy, phagostimulation and, in some cases, trail following or swarming behavior.

The end-user facilitates opening the package and placing the exposed mycelia contents in the vicinity of recent pest activity. For use as an attractant, extracts of the preconidial mycelium may also be utilized. It is envisioned that the fungal attractants and/or pesticides may be used in conjunction with any type of appropriate trap or attractant disseminator or delivery system that is known to the art.

By combining an extract of mycelium from a fungus having antimicrobial and/or antiviral properties with an extract from the preconidial mycelium of an entomopathogenic fungus, the unique mixture can serve as a unique combination for mitigating disease transmittance. A novel agent or treatment that kills the contagion but also severely harms the human host, for instance, is neither medically practicable nor commercially attractive. However, a novel agent that neutralizes the bacterium, protozoa or virus being carried by an insect is both medically and commercially significant. Moreover, if the preconidial entomopathogenic fungi attracts and simultaneously carries an infectious agent that controls the insect while also reducing internal pathogens harmful to animals and crops, disease transmission vectors can be limited, arrested, or re-directed using these unique combinations.

The present invention thus provides improved products and methods wherein the fungal mycelium acts as food and attractant and/or as an ingested or contact insecticide, palatable enough that insects will readily consume it even in the presence of competing food sources, or otherwise repellent materials, with high recruitment of other insects among insects that exhibit such behavior. This results in multiple visits to a highly attractive (and potentially virulent) food, thereby providing numerous individual insect and/or colony vectors of inoculation.

The present invention further provides these and other advantages with improved control of insect pests using fungal compositions (mycopesticides and mycoattractants) having strong attractant properties and placing these attractant preconidial fungi in or around an object or area to be protected. The present invention also provides insecticidal foods and baits that utilize, as a toxicant, relatively innocuous and naturally occurring materials as the active agent, so as to control insects carrying zoonotic diseases without undue effect on the ecology. Alternatively, the present invention provides attractants that can be utilized with bio-control agents, environmentally benign biopesticides, chemical control agents including insect toxicants and pesticides, human modified organisms, viruses and bacteriophages, physical control agents such as mechanical and electrical devices and combinations thereof. It is to be expected that the number of sub-inventions and applications obvious to those skilled in the relevant arts is limited only by imagination and time, and any such derivative inventions and applications should be considered to be part of the invention disclosed herein. New zoonotic diseases and new disease controlling technologies will emerge and the inventions described herein are likely to enhance many future technologies.

Still further objects and advantages of the present invention will become more apparent from the following detailed description and appended claims.

Before explaining the disclosed embodiments of the present invention in detail, it is to be understood that the invention is not limited in its application to the details of the particular products and methods illustrated, since the invention is capable of other embodiments, including those embodiments that have not yet been reduced to practice and tested. In addition, the terminology used herein is for the purpose of description and not of limitation.

DETAILED DESCRIPTION OF THE INVENTION

The concepts of "pathogens" and "pathogenic" (and the related "entomopathogens" and "entomopathogenic") have implications that extend well beyond the standard dictionary definition of "capable of causing disease or mortality." Some entomopathogenic fungi are widespread and cause no known affects whatsoever in their insect hosts; *Myrmicinosporidium durum* is illustrative of entomopathogenic fungi that cause few symptoms and are consequently hard to detect in the first place. Schmid-Hempel, P., *Parasites in Social Insects*, Princeton University Press, p. 83 (1998). Entomopathogenic fungi as used herein are those capable of infecting and parasitizing insects, regardless of their actual effect on the host. "Virulence" and "virulent strains" similarly have meanings extending beyond the dictionary definition of extremely infectious, malignant or poisonous. Parasite virulence and host resistance determine how host and parasite interact in ecological time and how they co-evolve. Virulence is often defined as an increase in the host mortality rate as a result of the parasite's presence. But reduced host fecundity, parasite replication rate within the host, and several other measures have also been used. Virulence should in principle also include instances where the behavior of the host is manipulated by the parasite to increase the probability of its successful transmission and where it places the individual host at greater risk. See Schmid-Hempel, supra, pp. 237-238. Here the terms virulent and virulence are used in a broad sense that encompasses all of these meanings. It will refer to processes which are caused by entomopathogenic fungi and which lead to a reduction in some component of the host's fitness or an increase in mortality. Virulence and resistance are therefore properties that emerge as a result of host-parasite interaction in a given environment. Expression of virulence is as diverse as the lifestyles and characteristics of the insect hosts and the entomopathogenic fungi themselves.

The present invention provides improved mycoattractants and mycopesticides (fungal mycelia utilized as insect and arthropod attractants or baits and/or insect or arthropod bio-pesticides, after mycology, the study of fungi) to control zoonotic diseases harbored by and vectored by insects and non-insect arthropods.

Laboratory procedures for testing entomopathogenic fungi often involve procedures inapplicable in the field, such as "dusting" of many or all of the insects with spores or forced contact with conidia in petri dishes (itself a form a stress). Social insects infected with mycopesticidal spores are often rejected or isolated from the general population, thus limiting the further spreading of the fungal disease. Wilson, E. O., *The Insect Societies*, The Belknap Press of Harvard University Press, pp. 103-119 (1974). For these and other reasons, conidia of entomopathogenic fungi have often been much more effective under laboratory conditions than in the field.

It was found that the "fragrance signature" of the mycopesticidal mycelium is a strong attractant to insects and arthropods prior to conidia formation. The genesis for these findings was the initial observation that the odor of the cultured mycelium was similarly pleasing to humans when preconidial and repellant after conidia formation; smell and the fragrance signatures of mycelium are utilized by the present inventor as indicators of the health of the mycelium in large scale production of gourmet and medicinal mushrooms, whereas "petri dish mycologists" and entomologists studying pathogenic fungi are typically trained not to sniff or inhale from the cultures. In fact, most mycologists are trained not to do so, as standard laboratory protocol, because such actions could be a threat to their health. It was noted such fragrance signatures are lost when mycelium is grown via liquid fermentation—this may be due to such fragrance signatures being "washed away" or due to the greatly reduced nutritional base available to the mycelium in liquid fermentation as compared to solid substrates such as grain or wood. "Outgassing" of $CO_2$ and attractant molecules by the mycelium is believed by the present inventor to be responsible for at least some portion of the attractant value. It was also noted that liquid fermentation utilizing a typical fermenter with bubbled air mixing will promote conidia formation, with such conidia production being even further promoted by the common commercial practice of utilizing bubbled or chemically generated oxygen.

In addition to the attractant properties and phagostimulatory (feeding stimulating) properties of preconidial mycopesticides, it was further found that pathogenic fungal control agents are much more effective when preconidial (pre-sporulation) mycopesticidal mycelium is ingested and/or contacted by the targeted insect as compared to conidia or post-sporulation mycelium/conidia offered to targeted insects for the purpose of infection by contact. The preconidial mycopesticidal mycelium is thought to be an effective attractant and/or pathogen, at least in part, because it is a preferred food, particularly for social insects and other fungi-feeding insects and arthropods such as mites.

The preconidial mycelium has been observed to be a preferred food source that stimulates "grazing" of the fungi on wood and/or grain, scattering of the fungus, and caching of the fungus by mushroom mites and other arthropods and social insects including termites, carpenter ants, and fire ants. Novel behaviors observed in the social insects include that of Formosan termites (*Coptotermes formosanus*) ignoring available wood while preferring to set up "housekeeping" in the mycelium, and fire ants and carpenter ants moving the preconidial fungi around the feeding arena and/or into nest chambers. Social insect colonies have been described as "factory fortresses." See Wilson, supra, (1974); Oster, G. F. and E. O. Wilson, *Caste and Ecology in the Social Insects*, Princeton University Press (1978); and Schmid-Hempel, supra, (1998). While it may be difficult for a parasite to "break into the fortress" and gain access to a colony, once inside, the opportunities abound (Schmid-Hempel, supra, p. 77 (1998)). Similarly, once the social insect defenses have been penetrated via the attractiveness of preconidial mycopesticidal mycelium, the opportunities abound for further inoculation and spread of the preconidial mycelium both orally and dermally, as well as optional introduction of other bio-control agents or chemical toxicants. Novel and unique features of the invention include the use of a mycopesticidal mycelium or extract as an attractant, the use of a mycopesticidal vector of parasitization that relies directly on hyphal fragments to infect both insects and/or social insect housing structures, the use of high levels of carbon dioxide to grow and maintain preconidial mycelium, the use of late sporulating strains to prolong the attractive preconidial state, the use of various methods to arrest development at the preconidial stage and/or to facilitate growth, packaging, shipping, and convenient application by an end user, and various improvements in methods of attracting, controlling, preventing, eradicating, and limiting the spread of disease vectoring insects and arthropods.

Preconidial mycelium has proven to be highly effective by ingestion or contact, with the exudate-excreting mycelial hyphae already being in a state of active growth when ingested or contacted. The preconidial mycelium is thought by the present inventor to function both as a "fungal food of infection" and as a contact pesticide. Efficacy as a contact pesticide is believed to be aided by the somewhat "sticky" nature of mycelium. While not wishing to be bound by any theories or hypotheses, the present inventor believes various possible vectors for further spread and growth of the preconidial mycelium include: incidental contact and adhesion; feeding and "sloppy eating" which may spread hyphae to insect cuticles; food caching; individual and social grooming; aerial transmission of hyphal fragments (as dry hyphal fragments are much less dense than spores, they easily become airborne and spread); inhalation; incidental contact; trophallaxis (exchange of liquid food); proctodeal trophallaxis (exchange of anal excrement by termites and others); cannibalism; mating; contact with cadavers; inoculation of housing structures; etc. Mycopesticidal species are thought by the present inventor to employ various pathogenic modes when transmitted via ingestion or contact with mycelial hyphae, including: infection via the cuticle, the tracheal openings, the alimentary canal, or wounds with resultant growth upon the insect and resultant depletion of host resources and/or damage or destruction of host tissue; production of antibiotics, antibacterials, and antiprotozoans with the resultant death of microflora within the gut; production of anti-fungal compounds affecting symbiotic and associated fungi; production of toxic substances by the entomopathogens; suppression or disruption of the immune system response; etc.

Since mites are non-insect arthropods and mites have long been observed as a pest to mushroom crops, both at the mycelial stage and when mushrooms subsequently form (Stamets, P. and Chilton, J., *The Mushroom Cultivator*, Agarikon Press, 1983), and since mites can be parasitized by entomopathogenic fungi, the use of preconidial mycelium of entomopathogenic fungi to attract and control mites, and the bacterial "blotch" they inflict to mushroom crops is an important new strategy for limiting losses in mushroom farms, or wherever mites inflict damage and cause bacterial diseases. The same methods described herein can be readily adapted for limiting mites, ticks and other arthropods and the diseases they spread to plants, thus protecting crops.

In utilizing wood and other cellulose containing materials, one preferred method is to grow the pre-sporulation mycopesticidal mycelium on wooden or other cellulosic materials "bait blocks" or "bait traps." Bait chips, blocks, or traps (or optionally other forms such as pellets, extruded pellets, mats, fabrics, ropes, etc.), optionally soaked with a malt solution, honey, or other sugar and/or nutrient solution, are infused and/or inoculated with preconidial mycopesticidal mycelia which then spread the infection to the targeted insect pests via any of the mycelium vectors described herein. Biodegradable bait traps may be made of, or have components made of various cellulosic, ligninic, celluloligninic, carbohydrate, and fiber materials including but not limited to: paper products and cardboard; wood and sawdust; corn cobs and cornstalks; chip board; fibers such as jute, flax, sisal, reeds, grasses, bamboo, papyrus, and coconut fibers; nut casings such as peanuts, almonds, walnuts, sunflower, pecans, etc.; seed hulls such as cottonseed hulls; agricultural products and byproducts such as hemp, cereal straws, sugar cane bagasse, soybean roughage, coffee wastes, tea wastes, cactus wastes, banana fronds, and palm leaves; industrial byproducts such as fiberized rag stock; combinations thereof, and numerous other forest agricultural, and industrial products and byproducts which will host mycelium and are degradable by mycopesticidal fungi. Where rapid biodegradability of the traps is desired, materials such as cardboard or paper may be utilized. For insects including carpenter ants or termites, cockroaches, etc., and arthropods such as bed bugs, mites and ticks, the bait blocks preferably contain channels, tunnels, grooves, ridges, holes or perforations specifically sized to allow entry by the targeted species and or its brood, pupae and/or larvae. Inoculation may, for example, be accomplished via grain in the channels and the blocks may optionally be layered or "wafered" together. A composite, layered or intertwined matrix of materials may be utilized, with one set of materials infused with the attractant extract of an entomopathogenic species and the other containing active or metabolically arrested preconidial mycelium. A multiplicity of such bait blocks or traps or barriers may be utilized to protect structures, agricultural locations, hospitals, dormitories, etc. A fungal matrix with a plurality of pre-sporulating mycopesticidal fungal species and/or extracts that are highly attractant to the targeted pest, combined with antimicrobial, antiprotozoan, and anti-viral ingredients, may be created so that the targeted pest is drawn close to a locus where the insect pest becomes infected and is harmed or killed by the selected fungi or via other means.

The wooden, cardboard, or lignin-cellulose baits and bait traps may optionally be frozen, dried or freeze-dried, or gaseously treated to arrest growth until activated by moisture and air exposure. Either the myceliated bait may be presented to the insect, with rehydration and recovery taking place, for example, within the central nests of social insects, or placed in the migration corridors of traveling insects and arthropods such as bed bugs. The bait block may be rehydrated prior to or during use or presented fresh.

The highly attractive nature of preconidial mycopesticidal mycelium indicates that essences extracted from preconidial mycelium of mycopesticidal fungi can be expected to be highly attractive in and of themselves, and in conjunction, associated compounds may possess innate antimicrobial or antiviral properties, and thereby similarly useful alone or in conjunction with biological, chemical, mechanical and/or electronic insect and arthropod control agents, useful as masking agents for otherwise repellant toxicants for pests, and useful as "distractants" in diverting pests away from sites that need protection. Such essences include extracts, concentrates, fragrances, derivatives, active constituents, etc. and may be prepared by methods known to the art including extraction with water, alcohols, organic solvents and supercritical fluids such as $CO_2$, etc. Extracts may also be prepared via steam distillation of volatile components, similar to the preparation of "essential oils" from flowers and herbs. Suitable alcohols include those containing from 1 to 10 carbon atoms, such as, for example, methanol, ethanol, isopropanol, n-propanol, n-butanol, 2-butanol, 2-methyl-1-propanol (t-butanol), ethylene glycol, glycerol, etc. Suitable organic solvents include: unsubstituted organic solvents containing from 1 to 16 carbon atoms such as alkanes containing from 1 to 16 carbon atoms; alkenes containing from 2 to 16 carbon atoms; alkynes containing from 2 to 16 carbon atoms; and aromatic compounds containing from 5 to 14 carbon atoms, for example, benzene, cyclohexane, cyclopentane, methylcyclohexane, pentanes, hexanes, heptanes, 2,2,4-trimethylpentane, toluene, xylenes, etc.; ketones containing from 3 to 13 carbon atoms such as, for example, acetone, 2-butanone, 3-pentanone, 4-methyl-2-pentanone, etc.; ethers containing from 2 to 15 carbon atoms such as such as t-butyl methyl ether, 1,4-dioxane, diethyl ether, tetrahydrofuran, etc.; esters containing from 2 to 18 carbon atoms such as, for example, methyl formate, ethyl acetate and butyl acetate; nitriles containing from 2 to 12 carbon atoms such as, for example acetonitrile, proprionitrile, benzonitrile, etc.; amides containing from 1 to 15 carbon atoms such as, for example, formamide, N,N-dimethylformamide, N,N-dimethylacetamide; amines and nitrogen-containing heterocycles containing from 1 to 10 carbon atoms such as pyrrolidine, 1-methyl-2-pyrrolidinone, pyridine, etc.; halogen substituted organic solvents containing from 1 to 14 carbon atoms such as, for example, bromotrichloromethane, carbon tetrachloride, chlorobenzene, chloroform, 1,2-dichloroethane, dichloromethane, 1-chlorobutane, trichloroethylene, tetrachloroethylene, 1,2-dichlorobenzene, 1,2,4-trichlorobenzene, 1,1,2-trichlorotrifluoroethane, etc.; alkoxy, aryloxy, cyloalkyl, aryl, alkaryl and aralkyl substituted organic solvents containing from 3 to 13 carbon atoms such as, for example, 2-butoxyethanol, 2-ethoxyethanol, ethylene glycol dimethyl ether, 2-methoxyethanol, 2-methoxyethyl ether, 2-ethoxyethyl ether, etc.; acids containing from 1 to 10 carbon atoms such as acetic acid, trifluoroacetic acid, etc.; carbon disulfide; methyl sulfoxide; nitromethane and combinations thereof. Extracts may also be prepared via sequential extraction with any combination of the above solvents. The extracts may optionally be combined with fixatives, enhancing agents, oils, alcohols, solvents, glycerin, water and other substances that aid in distributing the attractant and/or enhancing its fragrance value. Essences extracted from preconidial mycelium of mycopesticidal fungi can be used as protectants or distractants, luring insects away from a locus and preventing insect damage to a locus, habitat, structure, crop, animal, human, etc. Such attractant essences and extracts may be utilized with wicking agents, sprayers, etc. to enhance their effectiveness. Preliminary indications are that such attractant molecules are polar and thus best extracted with polar and/or hydrophilic solvents. The present invention in conjunction with the principles of chemical ecology and evolutionary biology raise the possibility that the entomopathogenic fungal species produce attractant molecules (or more likely, groups of attractant molecules) that have co-evolved over evolutionary time with species of insects or arthropods or groups thereof. Such attractant molecules, optimized for one species of insect or arthropod, may well show attractant properties to larger groups of insects or arthropods. Since all these fungi produce fatty acids, particularly linoleic acids, and other sterols, all have within them some of these attractant molecules. It will be apparent to those skilled in the art that numerous such molecules or groups of attractant molecules may be isolated and/or characterized from the preconidial fungi of the present invention and as such should be considered part of the present invention.

The preconidial mycelium or extracts thereof may be utilized solely as an attractant for various purposes. For example, preconidial mycelium may be utilized to affect insect or arthropod choice of geographical location, destructive and zoonotic disease bearing pests being attracted and distracted away from structures, agricultural plots, hospitals, army barracks, theaters, convention centers, hotels, schools, prisons, etc. Fungal species and strains particularly attractive to beneficial insects or arthropods such as beneficial mites, may be utilized to attract desired insect or arthropod species, the fungi acting as a biological catalyst to steer the course of the insect or arthropod community evolution. Alternatively, varying insects or arthropods may simply be attracted to occupy the environment and thus forestall pest invasions. It is known that virulence of entomopathogenic strains varies widely in the laboratory when tested via typical conidia based assays, with mortalities from 0% to 100% being recorded dependent upon such factors as number of conidia applied per insect or arthropod and the insect or arthropod species and the entomopathogenic species and strain being tested. Similar results may be expected for preconidial formulations, although a greater effectiveness in general may be expected since lack of virulence in the typical bioassay is often related to a failure of conidia to adhere to the insect or arthropod and/or failure of the conidia to germinate as discussed above. Thus strains of "pathogenic" or "entomopathogenic" fungal species may be selected which actually vary in virulence from non-pathogenic to relatively weakly virulent to strongly virulent. Non-virulent preconidial mycelium may be used to attract beneficial predator and parasitic insects or arthropods. Alternatively, non-virulent strains may be utilized as distractants, for example attracting Coccinellidae, the lady beetles, away from areas where they may be a pest (such as office buildings) and into "ladybug motels." Alternatively, virulent strains may be utilized as an olfactory attractant but made inaccessible with devices such as screens or slots.

The mycoattractants and/or mycopesticides disclosed herein may also be optionally enhanced by the use of other baits, foods, attractants, arrestants, feeding stimulants, sex pheromones, aggregating pheromones, trail pheromones, etc. For example, a bait box overgrown with preconidial mycopesticidal mycelium might contain other attractants, contact pesticides and antimicrobial, antiprotozoal, and antiviral ingredients.

Attractant preconidial or pre-sporulation mycelium (virulent, weakly virulent and/or non-virulent) or extracts may also be utilized in conjunction with other biological organisms, chemical pesticides and physical control agents as part of integrated pest management (IPM) systems that incorporate multiple pest control tools and seek to minimize pesticide inputs. The use of attractant fungi in combination with other insect control agents affords the advantage of attracting the targeted pest to a locus, which, by other treatments, results in sterility and/or death of the targeted insect or arthropod.

The weakened immune systems of pests exposed to pathogenic or virulent mycopesticidal organisms allows other beneficial parasitic and predator species to flourish. Such beneficial biological control agents include microbial pathogens, predator insects or arthropods (entomophagous insects or mites which eat other insects) and parasitic insects or arthropods (those which reproduce by laying eggs in or on any stage the host insect, from egg to adult), as well as non-insect predators such as birds and beneficial nematodes, spiders and mites. Examples of biological control agents include: entomopathogenic fungal species and their spores; *Bacillus thuringiensis, B. popilliae, B. subtilis*, and *Pseudomonas*; fire ant parasites (such as Phorid flies); fly parasites including wasps such as *Muscidifurax raptorellus* and *Spalangia cameroni*; hister beetles such as *Carcinops pumilio*; dung beetles including *Onthophagus* spp.; parasitic nematodes such as *Steinernema feltiae*; cockroach parasites such as *Anastatus tenuipes, Aprostocetus hagenowii, Comperia merceti* and nematodes; lacewings; ladybugs; bigeyed bugs; damsel bugs; praying mantises; *Trichogramma* wasps; beneficial mites; ant parasites; flea parasites; *lygus* bug parasites; mealybug; aphid and whitefly parasites and predators; caterpillar parasites; spider mite predators; looper parasites; diamondback and moth parasites; scale parasites and predators; mite parasites and predators; etc. Strains may be selected, utilizing those methods known to the art, for virulence against the targeted pest insects and arthropods, and/or non-virulence or weak virulence against predator insect species as well as such qualities as resistance to pesticides, etc. If desired, resistant predator or parasitic species may be selected for, bred and released to further control the targeted pest species. Blends of beneficial insect or arthropod attractant plants and habitat plants may also be utilized in combination with antimicrobial, antiprotozoal and antiviral agents. This multiplatform approach is not limited to just one pairing of fungus, one beneficial organism and one anti-disease component, but as many permutations as can be implemented for the purpose of creating an environmental equilibrium affording long-term protection of the inhabitants from other insects, arthropods, animals and plants. Other fungal attractants may also be optionally utilized. Thus, a combination of the preconidial mycelium of mycopesticidal species and Oyster mushrooms (*Pleurotus* and *Hypsizygus* species), the mycelium and mushrooms of which are very attractive to Phorid flies) might be utilized to attract phorid flies in the genus *Pseudacteon* that parasitize fire ants and leaf-cutter ants.

The preconidial mycopesticides (both virulent and non-virulent strains) and extracts may also be utilized as "masking agents" as well as attractants in conjunction with insect chemical control agents, toxicants and/or pesticides, thereby preventing aversion to other effective compounds that may otherwise repel the insects or arthropods. Chemical control agents include insect or arthropod toxicants, poisons, regulators and pesticides as well as the chemicals (semiochemicals) which mediate interactions between individuals of a insect or arthropod species (pheromones) or between co-evolved species (allelochemicals, such as kairomones and allomones). Residual (persistent), non-residual (nonpersistent), and solid, liquid, aerosol or fog contact chemical control agents include, by way of example but not of limitation: stomach poisons such as sulfluramid; pyrethrum extracts; natural and synthetic pyrethroids; parapyrethroids (non-ester pyrethroids) such as silafluofen, etofenprox and cyfluthrin; pyrethroid analogs such as fenvalerate, permethrin, phenproparthrin, fluvalinate, flucythrinate, fenproparthrin, cypermethrin, deltamethrin, tralomethrin, cycloprothrin, esfenvalerate and zeta-cypermethrin; allethrins; lethanes; nicotinyl compounds such as imidacloprid; phenylpyrazoles such as fipronil; amidinohydrazones such as hydramethylnon (a respiratory poison); abamectin (a mixture of avermectins, insecticidal or anthelmintic compounds derived from the soil bacterium *Streptomyces avermitilis*); Spinosad (spinosyn metabolites produced by *S. spinosa*); artemisinin from Artemesia plants; nitromethylenes; carbamates such as propoxur and fenoxycarb; organophosphates such as acephate and chlorpyrifos; pyriproxyfen; insect growth regulators; synthesis inhibitors; chitin synthesis inhibitors such as hexaflumuron and diflubenzuron; mineral acids such as boric acid; alcohols and organic solvents; elements such as sulfur; and combinations thereof. Such chemical control agents may optionally be combined with synergistic compounds that increase the toxicity and/or enhance the biological activity of another, for example by inhibiting the enzymatic detoxification of insecticides by microsomal oxidases or hydrolytic enzymes such as esterases. Examples of synergists include: methylenedioxyphenyl (MDP) compounds such as piperonyl butoxide, piperonal bis-(2,2-(butoxyethoxy)-ethyl)acetal, 1,2-methylenedioxynaphthalene, tropital (polyalkoxy acetal of piperonaldehyde) and sesamex; trisubstituted aliphatic and aromatic phosphates such as TOCP (tri-o-cresyl phosphate); a number of non-insecticidal carbamates; EPN(O-ethyl-O-p-nitrophenyl phenylphosphonothionate); sulfoxide; propynyl ethers; p-nitrobenzyl thiocyanate; 2-((4,6-dichloro-2-biphenylyl)-oxy)triethylamine; 2-(diethylamino)ethyl 2,2-diphenyl pentanoate; 2-propynyl 4-chloro-2-nitrophenyl ether; N-octyl bicycloheptane dicarboximide; and n-propyl isomer. Use of attractant or attractant/pesticidal preconidial mycelium or extracts, in combination with antibiotics and antivirals, enables the use of extremely small amounts of toxicant or pesticide to effectively control insect and arthropod populations and the diseases they transmit. Alternatively, sublethal doses of pesticides or toxicants may be included to enhance the activity and virulence of the mycopesticidal species; or pathogenic and virulent preconidial mycelium may be utilized as a preconditioning treatment, increasing the susceptibility to and/or potentiating the virulence of other agents (such as pesticidal chemicals, other mycopesticides, or bacteriological, plasmodial and viral compounds). Lethal or sublethal doses of insect and arthropod toxicant and antibiotic materials may optionally be encapsulated within an attractant extract or mycelia-impregnated (virulent or non-virulent) sheath, coating, covering, encapsulative material, protective and/or time degrading envelope, or the toxin may surround, cover or encapsulate a mycelial substance or extract of strong attractive and/or mycopesticidal properties, or such may be simply mixed.

The mycoattractants and mycopesticides of the present invention may also be combined with physical control agents. Physical control agents are devices that destroy insects directly or act indirectly as barriers, excluders, or collectors. Physical controls include the use of mechanical and electrical devices, heat, light, electricity, X-rays, lasers, and so on, to kill insects directly, reduce their reproductive capacity, or to attract them to something that will kill them. Various physical means may be employed to act as barriers to insect or arthropod movement. Sticky materials in which insects become hopelessly entangled may be used in the form of flypaper or coated objects and materials. Traps may be used for control, survey, and surveillance purposes. Control traps may be used in conjunction with mycoattractants and with some means of killing the insects or arthropods that enter (e.g., a pesticide or an electrically charged grid). Mosquito or bed nets, or bed bug traps can be impregnated to attract disease carrying insects or arthropods whereupon contact, they are trapped. If not trapped, the escaping insects and arthropods, post contact, may have their pathogenic payloads reduced and yet remain infectious carrying the entomopathogenic fungus to other insects and arthropods. This approach has many merits—as the insects and arthropods live after making contact, but now represent less of a threat for infection and disease transmission to humans and plants whilst still controlling populations of these problematic insects and arthropods.

The preconidial mycelium on manufactured, compressed pellets or granules, with or without additional liquid(s), can be used for applications in agricultural, forest, industrial and/or domestic settings, wherein the myceliated pellets become loci for attracting the target pests, and thus through contact become infected. Trends in mushroom spawn for gourmet and bioremediation purposes have long been evolving toward pelletized or granular spawn while mycopesticidal spore technology similarly has evolved toward granulated or spray formulations. Various forms of pelletized spawn, coated compositions, granules and dusts are known, including those formed from nutrients, with or without carriers and binders, such as peat moss, vermiculite, alginate gel, wheat bran, calcium salts, hydrophilic materials such as hydrogel, perlite, diatomaceous earth, mineral wool, clay, polymers, biopolymers and starch, including wettable powders, emulsifiable concentrates and/or biopolymer coatings, etc. Pelletized spawn is specifically designed to accelerate the colonization process subsequent to inoculation. Idealized pelletized spawn seeks a balance between surface area, nutritional content, and gas exchange and enables easy dispersal of mycelium throughout the substrate, quick recovery from the concussion of inoculation, and sustained growth of mycelium sufficient to fully colonize the substrate. See Stamets and Chilton, supra, pp. 141-142 and U.S. Pat. No. 4,551,165 (1985) to Warner, U.S. Pat. No. 4,668,512 (1987) to Lewis et al., U.S. Pat. No. 4,724,147 (1988) to Marois, et al., U.S. Pat. No. 4,818,530 (1989) to Marois, et al., U.S. Pat. No. 5,068,105 (1991) to Lewis, et al., U.S. Pat. No. 5,786,188 (1998) to Lamar, et al., and U.S. Pat. No. 6,143,549 (2000) to Lamar, et al. Liquid sprays include the above wettable powders and emulsifiable concentrates, water-dispersible granules, aqueous solutions, emulsions such as oil-in-water and water-in-oil emulsions, dispersions, suspoemulsions, microemulsions, microcapsules, etc. Wettable powders are formulations that are typically uniformly dispersible in water and also contain surface-active agents (surfactants) such as wetting agents, emulsifiers and dispersing agents. Emulsifiable concentrates are prepared with organic solvents and/or one or more emulsifiers. Sticking agents such as oils, gelatin, gums, tackifiers and adhesives may be used to improve the adhesion of the spray. Humectants may also be used to decrease the rate of evaporation, including for example glycols having from 3 to 10 carbon atoms and glycerin and solutes such as salts or sugars in water.

For large scale application, fabric or fiber cloths, landscaping cloths, geofabrics, soil blankets and rugs, mats, mattings, bags, gabions, fiber logs, fiber bricks, fiber ropes, nettings, felts, tatamis, bags, baskets, etc. made of biodegradable materials infused with preconidial mycelia of mycopesticidal species, combined with antimicrobial and antiviral agents, may be utilized as a mechanism for attracting, preventing, killing or limiting the spread of targeted insects and arthropods (or of attracting beneficial insects and arthropods) and zoonotic diseases. Thus, for example, barriers or "aprons" of mycopesticidal mycelium grown on straw, coconut fiber, wood, paper, cardboard or the other forestry and agricultural products, wastes and cellulose sources noted above might be placed around Oak trees to protect from beetles and introduced wilts such as *Phytophthora* and *Ceratocystis fagacearum* or around pine trees or stands to protect from destructive fungi and diseases carried by bark beetles. Similarly, such mycopesticidal aprons might be utilized to protect other trees, shrubs, grasslands, rivers and streams, estuaries, riparian zones, agricultural fields, gardens and crops, structures, communities, habitats and sensitive ecosystems. Such preconidial mycopesticidal aprons might alternatively be used to attract pest insects or arthropods to a site whereupon other biological, chemical, mechanical, electrical and/or other insect and arthropod reducing treatments become more effective. Conversely, creation of buffers utilizing non-virulent strains selected for attractiveness to beneficial insects can be used to attract beneficial species, which naturally parasitize problem insects and arthropods.

Alternatively, woodchips, grains, hydromulch and other substrates infused with preconidial mycelium may be utilized in spray hydroseeders or mobile hydroseeders. Agricultural equipment may be utilized to inoculate fields and agricultural wastes. The mycopesticidal fungi may also optionally be utilized in conjunction with saprophytic fungi and mycorrhizal fungi to enhance soils and agricultural yields ("companion cultivation" of beneficial fungi). Mycopesticidal species are also useful in the mycoremediation (fungal bioremediation) of various sites. As one example, reclaimed logging roads could become perimeter-barriers which could forestall and/or prevent beetle-plagues from devastating forestlands by infusing mycomats or hydromulches with species-specific pathogenic fungi (and optionally saprophytic and mycorrhizal fungi), combined with antimicrobial or antiviral agents, while simultaneously retaining other benefits of mycofiltration. Thus, mycopesticidal species such as *Metarhizium, Beauveria* and *Cordyceps*, mycorrhizal mycopesticidal fungi such as *Laccaria*, and myconematicidal saprophytic fungi such as *Pleurotus* might be combined with ectomycorrhizal and endomycorrhizal species and saprophytic fungi to provide simultaneous insect control, road reclamation and protection of streams from silt runoff and disease control. As *Hypholoma capnoides*, a premier wood chip decomposer, mycelium has been observed to be repellant to insects, stretches of insect repellant barriers may be combined with attractant mycopesticidal kill and/or control zones for insects such as wood-boring beetles. Similarly, control of agricultural runoff utilizing saprophytic fungi on agricultural wastes might be combined with the present mycoattractant and/or mycopesticidal applications, while in combination with antimicrobial and antiviral agents, to limit the spread of disease.

In general, preferred mycopesticidal species as pathogens are somewhat slow-acting (that is, not immediately fatal) so as to avoid bait shyness and to avoid learning effects in social insects and arthropods such as bed bugs before individuals have distributed mycelium to all other members of the colony. To effect control of the Formosan subterranean termite (*Coptotermes formosanus*) colonies, bait chemicals must kill slowly enough to allow foraging termites to return to the colony and spread the toxin to other colony members. Wright et al., "Growth response of *Metarhizium anisopliae* to two Formosan subterranean termite nest volatiles, naphthalene and fenchone," *Mycologia,* 92(1): pp. 42-45 (2000) and the references therein. Bait shyness and other colony defense mechanisms such as segregation or avoidance of infected nestmates or necrophoretic behavior by the workers (i.e., removal of dead nestmates) serve as a means of defense against the spread of such pathogens when the targeted insect or arthropod dies too quickly. For example, in general, queen fire ants will not feed on new foodstuffs until the food is first sampled by foragers or workers or members of expendable classes and deemed safe after a two or three day waiting period. Note, however, this general pattern may not always apply to the highly attractive mycoattractants and mycopesticides disclosed herein. Preconidial mycelium strains may be selected for virulence after an appropriate time period. In many applications it may be preferable to utilize a mixture or matrix of several species or strains of entomopathogenic fungus with different characteristics, maturation and growth rates including strains with delayed sporulation (and thereby prolonged attractant value) while in other applications a single species may be preferred. Similarly, with reference to a single species, a mixture of strains or a single strain may be utilized. A mixture of species and/or strains both allows the targeted insects to choose the species to which they are most attracted and provides for the possibility of simultaneous infection and insect plagues from multiple virulent species and strains. This makes tolerance or resistance of the insect or arthropod much more unlikely compared to just using one strain or antimicrobial agent.

Those skilled in the art will recognize that numerous entomogenous and entomopathogenic fungal species are known to the art and the above preconidial mycoattractant and mycopesticidal methods and products may be favorably applied to many or all such species, and it is the intent of the inventor that the invention be understood to cover such. Suitable entomopathogenic fungi include: the Deuteromycetes *Metarhizium, Beauveria, Paecilomyces, Hirsutella, Verticillium, Culicinomyces, Nomuraea, Aspergillus* and other fungi imperfecti; sexually reproducing fungi such as the Ascomycetes *Cordyceps, Ophiocordyceps, Ascosphaera, Torrubiella, Hypocrella* and its *Aschersonia* anamorph, and the *Pyrenomycete Laboulbenia hageni*; the Basidiomycetes such as *Laccaria, Pleurotus, Fomes, Fomitopsis, Hypsizygus, Piptoporus, Lenzites, Ganoderma*, and combinations thereof. The Entomophthoracae including *Entomophaga, Massospora, Neozygites, Zoophthora, Pandora* and other Phycomycetes are also considered to be within the scope of the invention. Also included are such entomopathogenic species that have been genetically modified to be more virulent (including those modified via mutagenesis, hybridization and recombinant DNA techniques).

By way of example, but not of limitation, mycopesticidal species include *Metarhizium anisopliae* ("green muscarine"), *Metarhizium flaviride, Beauveria bassiana* ("white muscarine"), *Beauveria brongniartii, Paecilomyces farinosus, Paecilomyces fumosoroseus, Verticillium lecanii, Hirsutella citriformis, Hirsutella thompsoni, Aschersonia aleyrodis, Entomophaga grylli, Entomophaga maimaiga, Entomophaga muscae, Entomophaga praxibulli, Entomophthora plutellae, Zoophthora radicans, Neozygites floridana, Nomuraea rileyi, Pandora neoaphidis, Tolypocladium cylindrosporum, Culicinomyces clavosporus* and *Lagenidium giganteum*, the wide variety of *Cordyceps* (and *Ophiocordyceps*) and its ascomycetous forms including *Cordyceps variabilis, Cordyceps facis, Cordyceps (Elaphocordyceps) subsessilis, Cordyceps myrmecophila, Cordyceps sphecocephala, Cordyceps entomorrhiza, Cordyceps gracilis, Cordyceps militaris, Cordyceps washingtonensis, Cordyceps melolanthae, Cordyceps ravenelii, Cordyceps unilateralis, Cordyceps sinensis* and *Cordyceps clavulata*, and mycorrhizal species such as *Laccaria* bicolor. Other mycopesticidal species will be apparent to those skilled in the art.

The concepts of "preconidial" and "spores" or "conidia" are complex, containing a number of different forms and specialized structures for reproduction of the fungi. Many fungi are pleomorphic, that is, one fungus may produce several sorts of spores, which may or may not be coincident in time. With regard to the sexually reproducing *Cordyceps, Laccaria* and other "fungi perfecti," preconidial or pre-sporulation refers to the pre-fruiting state. The term "preconidial" or "pre-sporulation" has a somewhat different meaning with regard to the sexually reproducing fungi than with most other entomopathogenic fungi, as sexually reproducing fungi are "fungi perfecti" or mushroom fungi, whereas the non-mushroom fungi such as *Beauveria* and *Metarhizium* are the more primitive "fungi imperfecti." The situation is complicated by the fact that entomophthoralean fungi have complex life cycles involving non-sexual conidia and sexual resting spores. The situation is further complicated by the fact that some or all *Cordyceps* fungi are dimorphic and have a teleomorph (the sexual perfect form or morph, e.g. that characterized by sexual spores including ascospores and basidiospores) and one or more anamorphs (the asexual imperfect form or morph, e.g. characterized by the presence or absence of conidia) with conidial stages within the imperfect fungal genera including *Beauveria, Metarhizium, Paecilomyces,*
*Hirsutella, Verticillium, Aspergillus, Akanthomyces, Desmidiospora, Hymenostilbe, Mariannaea, Nomuraea, Paraisaria, Tolypocladium, Spicaria (=Isaria)* and *Botrytis*. For example, *Cordyceps subsessilis* is the perfect form of *Tolypocladium inflatum*, an anamorph (imperfect) form which produces cyclosporin. Hodge et al., *Mycologia* 88(5): 715-719 (1996). *Cordyceps militaris* (Fr.) Lk. is also thought to be dimorphic, the conidial stage of which is believed to be a *Cephalosporium. Cordyceps unilateralis* seems specific on the Camponotinii, while *Hirsutella sporodochialis* is probably an anamorph of *Cordyceps unilateralis* specific on *Polyrhachis*. Schmid-Hempel, supra, p. 43. The situation is further complicated in that conidia, without asci, have often been observed in *Cordyceps* by the inventor. DNA studies are expected to better elucidate these relationships. As used herein, unless otherwise specified, preconidial or pre-sporulation mycelium of sexually reproducing fungi refers to the pre-sporulation mycelial stage of the mushrooms, including any preconidial imperfect stages and any preconidial sclerotia or microsclerotia.

It is further expected that the preconidial products and methods may, with no more than routine experimentation, prove useful against presocial, parasocial, subsocial and nonsocial insects and arthropods including semisocial, quasisocial, communal and solitary insect pests such as: cockroaches including American, German, Surinam, brown-banded, smokybrown, and Asian cockroaches; grasshoppers and locusts; crickets including mole cricket, Mormon crickets (actually a long-horned grasshopper); beetles, beetle grubs and beetle larvae including Colorado potato beetle (*Leptinotarsa decemlineata*) and other potato beetles, Mexican bean beetle, Japanese beetle, cereal leaf beetle, darkling beetle (lesser mealworm); moths including Gypsy moths (*Lymantria dispar*) and Gypsy moth larvae, diamondback moths (*Plutella xylostella*), codling moth (*Laspeyresia pomonella*), Douglas fir tussock moth (*Orgyia pseudotsugata*), western spruce budworm (*Choristoneura occidentalis*) and grape berry moths (*Lobesia lobina*); flies and fly larvae; springtails; large centipedes; shield centipedes; millipedes; European corn borers (*Ostrinia nubilalis*); Asiatic corn borers; caterpillars including velvetbean caterpillar (*Anticarsia gemmatalis*) and other caterpillars and larvae of the Lepidoptera; whiteflies (*Dialeurodes* and *Bemisia* spp.) including sweet potato whiteflies, and silverleaf whiteflies; thrips (*Thrips* spp.) including melon thrips (*Thrips palmi*), and western flower thrips (*Frankliniella occidentalis*); aphids including Russian wheat aphid; spider mites (*Tetranychus* spp.); mealybugs including citrus mealybug (*Planococcus cite*) and *solanum* mealybug (*Pseudococcus solani*); boll weevils, black vine weevils (*Otiorhynchus sulcatus*), European pecan weevils (*Curculio caryae*); mosquitoes; wasps; cotton fleahoppers; pasture scarabs such as *Adoryphorus couloni* and other Scarabaeidae; spittle bug (*Mahanarva posticata*); corn earworm (*Helicoverpa zea*); American bollworm (*Heliothis armigera*); armyworms including *Pseudaletia unipuncta*, fall armyworm (*Spodoptera frugiperda*), southern armyworm (*Spodoptera eridania*), beet armyworm (*Spodoptera exigua*), and yellowstriped armyworm (*Spodoptera ornithogalli*); black cutworm (*Agrotis ipsilon*); tobacco hornworm (*Manduco Sexta*); tobacco budworm (*Helicoverpa* (syn. *Helicoverpa*) *virescens*); sugar cane froghopper; rice brown planthopper; earwigs; loopers including cabbage looper (Trichoplusia nib soybean looper (*Pseudoplusia includens*), forage looper (*Caenurgina erechtea*) and celery looper (*Anagrapha falcifera*); cabbageworms including the imported cabbageworm (*Pieris rapae*) and the European cabbageworm (*Pieris brassicae*); tomato pinworm (*Keiferia lycopersicella*);

tomato hornworm (*Manduca quinquemaculata*); leafminers (*Liriomyza* spp.); cotton leafworm (*Alabama argillacea*); corn rootworm; garden webworm (*Achyra rantalis*); grape leaffolder (*Desmia funeralis*); melonworm (*Diaphania hyalinata*); pickleworm (*Diaphania nitidalis*); achemon sphinx (*Eumorpha achemon*); sweet potato hornworm (*Agrius cingulata*); whitelined sphinx (*Hyles lineata*); lygus bugs (*Lygus* spp.); chinch bugs including *Blissus leucopterus* and false chinch bugs; sow bugs; pill bugs; citrus rust mite; pill wood lice; wheat cockchafer; white grubs and cockchafers; *Hoplochelis marginalis* and *Melolontha melontha*; storage pests such as *Prostephanus truncatus* and *Sitophilus zeamais*; soil insects; and various other insect pests in the orders Isopoda, Diplopoda, Chilopoda, Symphyla, Thysanura, Collembola, Orthoptera, Dermaptera, Anoplura, Mallophaga, Thysanoptera, Heteroptera, Homoptera, Lepidoptera, Coleoptera, Diptera, Siphonaptera, Thysaoptera, Acarina, Arachnida, etc. and the families Plutellidae, Acrididae, Tettigoniidae, Gryllidae, Cryllotalpidae, Pyralidae, Sphingidae, Noctuidae, Pyralidae, Xylophagidae, Scarabaeidae, Scolytidae, Platypodidae, Lymexylidae, Nitidulidae, Pseudococcidae, Aphidae, Dalphacidae, Cicadellidae, Cercopidae, Aleyodidae, Coccoidea, etc. It will be recognized that the insects listed above are representative examples of insects and arthropods which may be attracted and/or controlled according to the present invention, but such listing is not intended as a limitation to certain species as numerous other insect and arthropod species to which the invention may be applied will be apparent to those skilled in the art.

It will be noted from the discussion above and examples and results below that attractiveness, pathogenicity and virulency toward the targeted insect are dependent in some degree upon factors including choice of mycopesticidal species, host range and specificity, selection of a strain within that species and selection of substrate. Entomopathogenic fungi also vary greatly in host specificity. Some entomopathogenic fungi are highly specific, such as *Pandora neoaphidis*, which is restricted to aphids. Other entomopathogenic fungi have wide host ranges, such as *Beauveria bassiana*, which is known to infect over 700 species of arthropods. Other species with wide host ranges include *Metarhizium anisopliae, Paecilomyces farinosus* and *Zoophthora radicans*. However, in the laboratory, isolates of fungi with wide host ranges are generally most virulent to the host from which they were first isolated; certainly their host range is much more restricted than that of the species to which they belong. Goettel et al., "Safety to Nontarget Invertebrates of Fungal Biocontrol Agents," in: Laird et. al. (eds.) *Safety of Microbial Insecticides*, pp. 209-232 (1990). Furthermore, fungi with wide host ranges are frequently even more specific under field conditions. There are reports of fungi attacking only one host even though closely related host species are present. Discrepancies between reports of social insect host specificity may be related to a general difference between tropical vs. temperate habitats rather than to the specific fungi and social insect species involved. Schmid-Hempel, supra at p. 44. Such specificity is thought to be due to the complex biotic and abiotic interactions in the field. This indicates that it should be possible, using no more than routine experimentation and bioassays of mycopesticidal strains and of the appropriate orders, families, genera, species and varieties of targeted pest insects, to isolate and use strains and substrates wherein the desired characteristics are maximized with respect to either a targeted insect or targeted insect group, thereby producing a species-specific, genus-specific, family-specific or order-specific entomopathogenic host specific fungal strain. Such entomopathogenic strains selected for host range and specificity may be similarly selected for minimal or no infection, or virulence towards beneficial insects or non-targeted insects.

Example 1

Attracting and Controlling Mosquitoes, which can Carry Viruses

Figure 1:
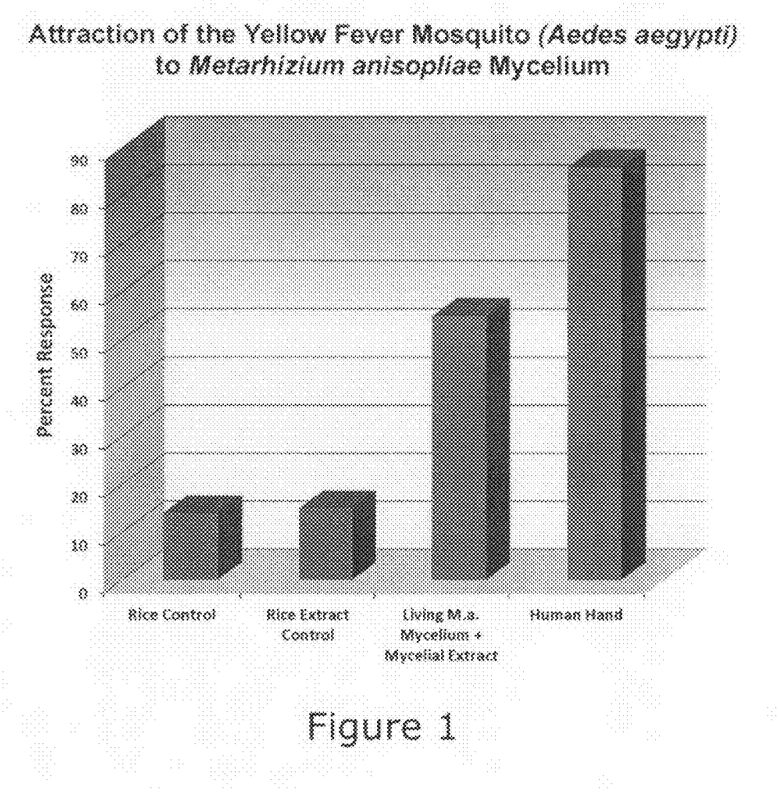
FIG. 1 is a graph showing attraction of the Yellow fever mosquito (*Aedes aegypti*) to *Metarhizium anisopliae* pre-conidial mycelium and extract.

Rice colonized by preconidial mycelium of *Metarhizium anisopliae* (ATCC #62716, and "F52") fungus clearly attracted *Aedes aegypti* females. Using an olfactometer in choices tests, the mycelium grown on rice attracted the female mosquitoes significantly over the controls. By comparison in the olfactometer, response of these host-seeking *Aedes aegypti* to a hand is about 83% to $CO_2$ (Allan et al. 2006). Combining the preconidial mycelium and the extracts from the same mycelium resulted in attractancy of mosquitoes to more than 80% equivalency to a human hand, far more so than the mycelium or extract alone. Since the actively growing mycelium is also outgassing carbon dioxide (but the extract does not), the added attractiveness of using an ethanolic/water extract is significant. *Aedes* mosquitoes spread viruses such as yellow fever, Chikungunya fever, and Dengue fever. Adding antiviral medicines previously proven useful, or yet to be discovered, to the extracts or mycelium of the preconidial entomopathogenic fungus, would abate the spread of disease, whether or not insect mortality occurred.

See FIG. 1 showing attraction of the Yellow fever mosquito (*Aedes aegypti*) to preconidial *Metarhizium anisopliae* mycelium and extract.

Example 2

Attracting and Controlling Mosquitoes, which can Carry Malaria Protozoa

Prepare mycelium and extracts by the methods described herein. Mix in, either individually or in combination, DDT, chemical pesticides, purified artemesinin or its crude, less expensive precursors, with the extracts and mycelium from preconidial entomopathogenic fungi such as *Metarhizium anisopliae* to bait and control stations, nets, or into standing water. Place these mixtures in environments where the mosquitoes exist, including *Anopheles gambiae* or any of its 30-40 species relatives, all of which carry Malaria protozoa (*Plasmodium falciparum*).

Example 3

Attracting and Controlling Flies, which can Carry Viruses

Prepare the preconidial mycelium and extracts of the preconidial mycelium *Metarhizium anisopliae* according the methods described previously and blend with ribavirin, oseltamivir, and other antiviral drugs in pure or crude form to preconidial extracts and/or mycelium of *Metarhizium anisopliae* to attract house flies or blow ("blue bottle") flies and, upon contact or ingestion, reduce the viral loads of flu viruses they carry, thus reducing their contagiousness.

Example 4

Attracting and Controlling Flies, which can Carry Bacterial and Protozoa Pathogens Prepare the preconidial mycelium and extracts of the preconidial mycelium *Metarhizium anisopliae* according the methods described previously and blend with antimicrobial agents active against bacteria and protozoa. Use this blend to attract Tsetse fly carrying species of the protozoan genus *Trypanosoma* causing often-fatal "sleeping sickness." Use this blend to attract house flies (*Musca domestica*) and Blow Flies (Calliphoridae, *Calliphora vicina*, and related species), which carry the pathogens *Staphylococcus aureus*, *Streptococcus pyogenes*, *Bacillus anthracis*, *Listeria*, *Salmonella*, *Clostridium*, and Enterococci, which subsequent to contact, result in reduced pathogen payloads and infectivity.

Example 5

Attracting and Controlling *Cimex* Species (Bed Bugs), which Carry Pathogenic Bacteria Prepare the preconidial mycelium and extracts of the preconidial mycelium *Metarhizium anisopliae* according the methods described previously and blend with antimicrobial agents active against *Staphylococcus aureus* bacteria or antiviral agents active against meningitis causing viruses and bacteria. Use this blend to attract and control bed bugs resulting in reductions in their levels of *Staphylococcus aureus* bacteria or meningitis causing viruses, making them less contagious, reducing infectivity.

Figure 2:
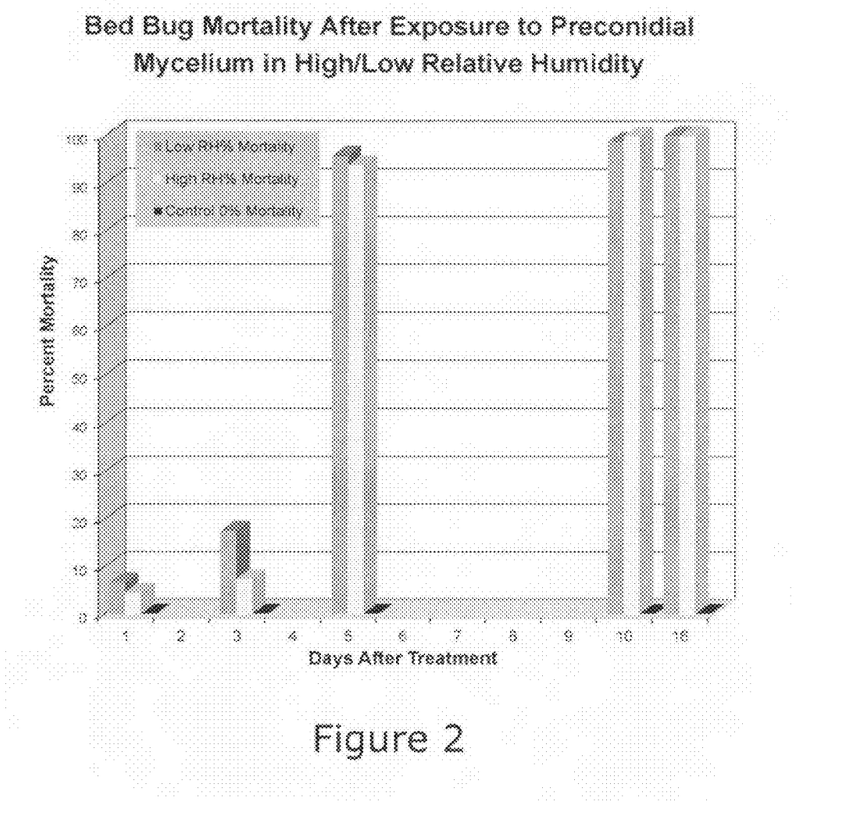
FIG. 2 is a graph showing bed bug mortality after exposure to preconidial mycelium in high/low relative humidity.

See FIG. 2 showing bed bug (*Cimex* species) mortality under high/low relative humidity conditions subsequent to contact with preconidial mycelium of *Metarhizium anisopliae* grown on a fabric. Those few bed bugs that survived after 5 days from initial contact, succumbed 10 and 16 days later.

Example 6

Attracting and Controlling Lice and Ticks, which Carry Pathogenic Bacteria

Prepare the preconidial mycelium and extracts of the preconidial mycelium *Metarhizium anisopliae* according the methods described previously and blend with antimicrobial agents active against *Rickettsia* spp. (the cause of Rocky Mountain Spotted fever), *Bartonella vinsonii* and *B. henseiae* causing intramuscular infections and/or *Borrelia burgdorferi* causing Lyme disease. Use this blend to attract and control pathogen bearing lice and ticks, resulting in reductions in their levels of pathogenic bacteria, making them less contagious, reducing infectivity.

Example 7

Attracting and Controlling Fleas, which Carry Pathogenic Bacteria

Prepare the preconidial mycelium and extracts of the preconidial mycelium *Metarhizium anisopliae* according the methods described previously and blend with antimicrobial agents active against the bacteria *Yersinia pestis* causing bubonic plague. Use this blend to attract and control pathogen-bearing fleas, resulting in reductions in their levels of pathogenic bacteria, making them less contagious, reducing infectivity.

Example 8

Attracting and Controlling Midges, which Carry Pathogenic Viruses

Prepare the preconidial mycelium and extracts of the preconidial mycelium *Metarhizium anisopliae* according the methods described previously and blend with antiviral agents active against viruses (Blue tongue virus to cattle, epizootic hemorrhagic diseases). Use this blend to attract and control pathogen-bearing midges, resulting in reductions in their levels of pathogenic bacteria, making them less contagious, reducing infectivity.

Example 9

Attracting and Controlling Flies Carrying Viruses

Prepare the preconidial mycelium or extracts of the preconidial mycelium *Metarhizium anisopliae* according the methods described previously and blend with extracts of mushroom mycelium such as *Cordyceps variabilis*, *Cordyceps facis*, *Cordyceps* (*Ophiocordyceps*) *subsessilis*, *Cordyceps myrmecophila*, *Cordyceps sphecocephala*, *Cordyceps entomorrhiza*, *Cordyceps gracilis*, *Cordyceps militaris*, *Cordyceps washingtonensis*, *Cordyceps melolanthae*, *Cordyceps ravenelii*, *Cordyceps unilateralis*, *Cordyceps sinensis*, *Cordyceps clavulata*, *Fomitopsis officinalis*, *Fomitopsis pinicola*, *Fomitporia robustus*, *Piptoporus betulinus*, *Trametes versicolor*, *Trametes elegans*, *Ganoderma lucidum*, *Ganoderma applanatum*, *Ganoderma annularis*, *Ganoderma oregonense*, *Ganoderma resinaceum*, *Ganoderma tsugae*, *Heterobasidion annosum*, *Inonotus obliquus*, *Antrodia camphorate*, *Rigidoporus ulmarius*, *Perenniporia fraxinophila*, *Psilocybe cyanescens*, *Psilocybe azurescens*, *Psilocybe cubensis* and other mushroom-derived antiviral drugs in pure or crude form to attract fungus gnats, house flies or Blow ("blue bottle") flies and upon contact, reduce the viral loads they carry, thus reducing their contagiousness.

Figure 3:
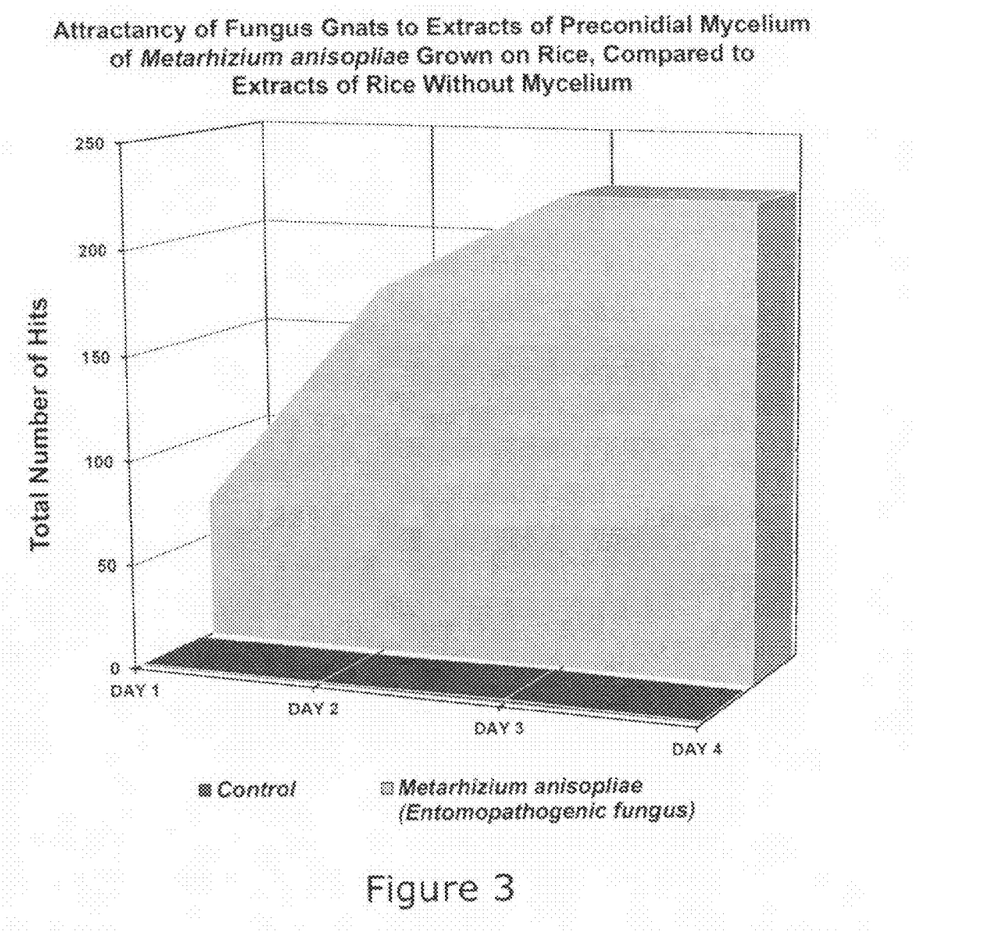
FIG. 3 is a graph showing attractancy of fungus gnats to extracts of pre-sporulating mycelium of *Metarhizium anisopliae*.

See FIG. 3, phorid flies fungus gnats, attracted to extract of preconidial mycelium of entomopathogenic fungus *Metarhizium anisopliae* grown on rice, compared to the rice control.

Example 10

Attract and Control Flies to Insect and Arthropod Control Devices

Add preconidial extracts and/or mycelium of *Metarhizium anisopliae* (prepared according the methods described previously, and blended with antimicrobial and antiviral agents) to insect and arthropod trapping and killing devices such as 'bug zappers' (BASF's Vector), forced airflow (fan) trapping systems, $CO_2$ emitters, gas toxicants, laser target-and-kill systems, soaping systems, sticky mats, "Velcro" like hook-and-spike entanglement devices, and bug nets, resulting in reducing the threat of insects and arthropods and the contagions and zoonotic diseases that they carry.

Example 11

Attracting and Controlling Disease-Bearing Arthropods with Cellulosic Materials

Add preconidial extracts and/or mycelium of *Metarhizium anisopliae* (prepared according the methods described previously, and blend with antimicrobial and antiviral agents) to fabric cloths, burlap sacks, wood chips or straw, to attract insects and arthropods carrying pathogens that results in a reduced pathogen load within these insects and arthropods subsequent to contact.

Example 12

Attracting Mosquitoes to Attract Disease Carrying Bats and Birds

Prepare the preconidial mycelium and extracts of the preconidial mycelium *Metarhizium anisopliae* according the methods described previously and blend with complex mixtures of numerous antimicrobial and antiviral agents active against the contagions carried by disease carrying bats and birds. By using complex mixtures of numerous antimicrobial and antiviral agents, multi-drug resistance is less likely as the contagions would have to adapt not to one agent but many. Use this blend to attract ticks, mites, mosquitoes and other flying insects, which in turn will attract and control the movement of bats and birds. The ingestion of the arthropods or insects, now carrying antimicrobial and antiviral agents, can then reduce the pathogen payload of the bats and birds, thereby reducing contagion risk.

Example 13

Blending Antiviral Drugs with Extracts and Mycelium of Preconidial Entomopathogenic Fungi Blend the extracts or mycelia of preconidial entomopathogenic fungi with the less expensive antiviral drug precursors, expired antiviral drugs, prodrugs or antiviral drugs such as Abacavir, Aciclovir, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Famciclovir, Fomivirsen, Fosamprenavir, Foscarnet, Fosfonet, Ganciclovir, Ibacitabine, Immunovir, Idoxuridine, Imiquimod, Indinavir, Inosine, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir (Tamiflu), Peginterferon alfa-2a, Penciclovir, Peramivir, Pleconaril, Podophyllotoxin, Protease inhibitors, Raltegravir, Reverse transcriptase inhibitor, Ribavirin, Rimantadine, Ritonavir, Pyramidine, Saquinavir, Stavudine, Tea tree oil, Tenofovir, Tenofovir disoproxil, Tipranavir, Trifluridine, Trizivir, Tromantadine, Truvada, Valaciclovir (Valtrex®), Valganciclovir, Vicriviroc, Vidarabine, Viramidine, Zalcitabine, Zanamivir (Relenza®) and Zidovudine to attract disease carrying insects and arthropods, and upon contact or ingestion, reduce their pathogenic payloads, thus reducing their contagiousness, and limiting disease transmission.

Example 14

Blending Antibacterial Drugs with Extracts and Mycelium of Preconidial Entomopathogenic Fungi Blend the extracts or mycelia of preconidial entomopathogenic fungi with the less expensive antibacterial drug precursors, expired antibacterial drugs, or antibacterial drugs such as Amoxycillin, Ampicillin, Cipro, Duricef, Erythromycin, Floxin, Levaquin, Roxithromycin, Suprax, and Zithromax to attract disease carrying insects and arthropods, and upon contact or ingestion, reduce their pathogenic payloads, thus reducing their contagiousness, and limiting disease transmission.

Example 15

Blending Antiviral Drugs with Extracts and Mycelium of Preconidial Entomopathogenic Fungi to Protect Plants from Viral Diseases Blend the extracts or mycelia of preconidial entomopathogenic fungi with antiviral drugs or prodrugs that protect plants to attract disease carrying insects and arthropods, and upon contact or ingestion, reduce their pathogenic payloads, thus reducing their contagiousness, and limiting disease transmission, thus protecting plants.

Leafhoppers, and white flies, which transmit viruses to plants, can be attracted to the extracts and mycelium of preconidial entomopathogenic fungi and limit viral disease transmission. Moreover, when antiviral drugs or their less pure, crude precursors are employed in combination with the extracts of preconidial entomopathogenic mycelium or with the preconidial mycelium of entomopathogenic fungi, the viral transmission threat from white flies and leafhoppers is reduced or eliminated, thus saving crops from the damaging effects of viruses. Two exemplary examples are the beet leafhopper, *Circulifer tenellus*, which spreads curly top virus; *Macrosteles facsifrons* spreads mycoplasma to hundreds of plants, including many vegetables. Additionally, hundreds of species in family Cicadellidae transmit plant diseases, many of which are viruses.

Example 16

Blending Extracts and Mycelium of Preconidial Entomopathogenic Fungi with Genetically Modified or Transgenic Organisms Blend extracts of preconidial entomopathogenic mycelium or with the preconidial mycelium of entomopathogenic fungi to attract and control insects and arthropods that transmit contagions that harm plants, and which results in making contact with genetically modified or transgenic organisms, further resulting in the protection of plants from viruses and other contagions carried by insects and arthropods.

Example 17

Blending Extracts and Mycelium of Preconidial Entomopathogenic Fungi with Bacteriophages to Limit Disease Transmission Blend extracts of preconidial entomopathogenic mycelium with the preconidial mycelium of entomopathogenic fungi, to attract and control insects and arthropods that transmit contagions that harm plants and animals, with bacteriophages, thus protecting plants and animals by the effect of the bacteriophages' ability to reduce or fend off transmittable diseases.

Example 18

Blend extracts and mycelium of *Fomitopsis officinalis, Ganoderma resinaceum, Ganoderma lucidum, Grifola frondosa, Inonotus obliquus, Piptoporus betulinus, Trametes versicolor, Pleurotus ostreatus* and other basidiomycetous mushroom-forming fungi possessing antiviral, antibacterial or antiprotozoal properties with the extracts of preconidial entomopathogenic fungi to protect animals from viral, bacterial, and protozoal diseases.

Example 19

A house was treated with preconidial mycelium of *Metarhizium anisopliae* grown on brown rice. Foraging carpenter ants came into contact with bait stations containing the preconidial mycelium of *Metarhizium anisopliae*. Subsequently, the carpenter ant colony infecting the house, which was about 15 feet away, lost their zeal and/or ability to forage far away from the nest to the house. Even if the colony was or is not killed, the treatment using preconidial mycelium of *Metarhizium anisopliae* resulted in limiting their range of exploration, reducing their travel and foraging behavior to the nearby proximity. In effect, after treatment, the colony is exhibiting new behavior—staying more proximate with a new, smaller territorial range, with fewer individuals, thus making it easier to protect people and structures.

No limitations with respect to the specific embodiments and examples disclosed herein are intended or should be inferred, as the examples and embodiments are representative only. While examples and preferred embodiments of the present invention have been shown and described, it will be apparent to those skilled in the art, or ascertainable using no more than routine experimentation, that many changes and modifications may be made without departing from the invention in its broader aspects. The appended claims are therefore intended to cover all such changes, modifications and equivalents as fall within the true spirit and scope of the invention.

I claim:

1. An entomopathogenic fungal composition for attracting and controlling insects and arthropods that carry diseases comprising a preconidial preparation of an entomopathogenic fungus, wherein preconidial mycelium is cultured from a sector of an entomopathogenic fungus culture displaying the preconidial mycelium rather than those sectors displaying post-conidial mycelium to produce a preconidial mycelium, wherein the preconidial preparation is selected from the group consisting of preconidial mycelium cultured on a solid substrate, extract of preconidial mycelium cultured on a solid substrate and combinations thereof, and wherein the entomopathogenic fungus is selected from the group consisting of *Metarhizium* and *Beauveria* and combinations thereof.

2. The entomopathogenic fungal composition of claim 1 wherein the composition further comprises conidia of entomopathogenic fungi and wherein the attractive properties of preconidial mycelium, in the form of fungal filaments and hyphal fragments and extracts thereof, overcomes the repellent properties of conidia based compositions, thus making fabric cloths and sticky mats useful for catching and controlling insects and arthropods selected from the group consisting of mosquitoes and bed bugs.

3. The composition of claim 1 wherein the entomopathogenic fungal composition further comprises entomopathogenic conidia and the preconidial mycelium attractive properties are more powerful than the repellent properties of the conidia, resulting in attractancy to locations populated by preconidial preparations and conidia.

4. The entomopathogenic fungal composition of claim 1 wherein a strain of the entomopathogenic fungus is chosen for a characteristic selected from the group consisting of preconidial attractiveness to a targeted insect, phagostimulation, slowness to sporulate, mycelial pathogenicity and virulence, lack of virulence and pathogenicity, host specificity for targeted pest insects, time to insect death, mortality rate for pathogenic and virulent strains, low mortality rate of non-targeted insects, the proportion of kill of each life stage including larvae, pupae, nymphs, workers, soldiers and royalty, high transmission rates, growth rate and speed of colonization of substrates, sensitivity and response to high and low carbon dioxide levels, recovery from metabolic arrest, recovery from transportation, stress tolerance, preferred temperature and humidity conditions, microflora sensitivity, ability to surpass competitors, adaptability to single component, formulated and complex substrates, high production of attractant extracts, genetic stability, non-sensitivity and resistance to chemical control agents, post-sporulation pathogenicity and combinations thereof.

5. The entomopathogenic fungal composition of claim 1 wherein the insects are selected from the group consisting of animal biting insects, plant biting insects, mushroom biting insects, mosquitoes, flies, bed bugs, fleas, midges, lice, triatomid bugs and leafhoppers and wherein the arachnids are selected from the group consisting of animal-biting arachnids, non-animal biting arachnids, spiders, ticks and mites.

6. The entomopathogenic fungal composition of claim 1 wherein the insects are selected from the group consisting of malaria-carrying mosquitoes, virus-carrying mosquitoes, contagion-carrying flies, contagion-carrying ants, contagion-carrying bed bugs, contagion-carrying fleas, contagion-carrying midges, contagion-carrying lice, contagion-carrying triatomid bugs and combinations thereof and the arachnids are selected from the group consisting of virus-carrying ticks, contagion-carrying ticks, contagion-carrying mites and combinations thereof.

* * * * *